Figure 1:
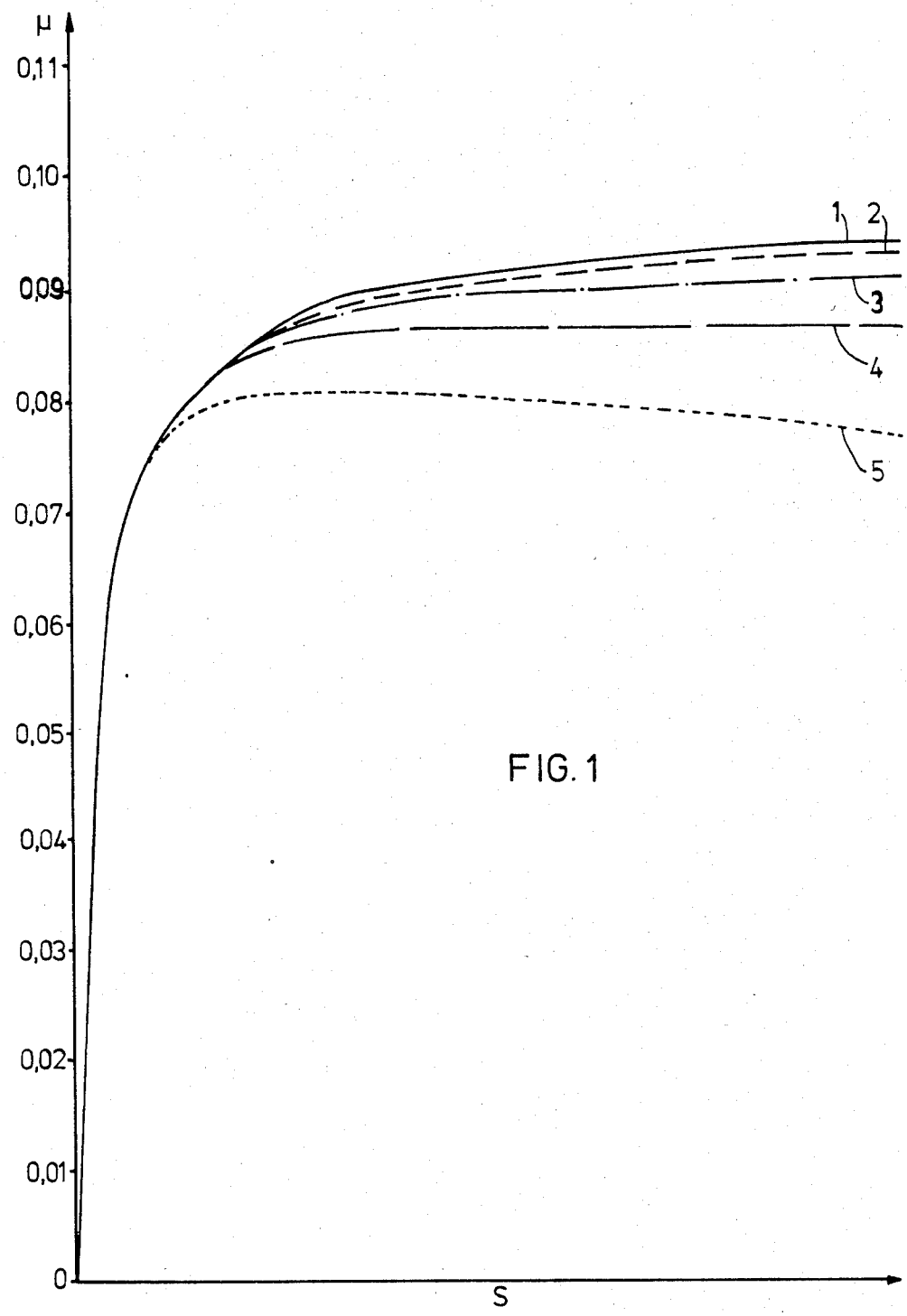
Figure 2:
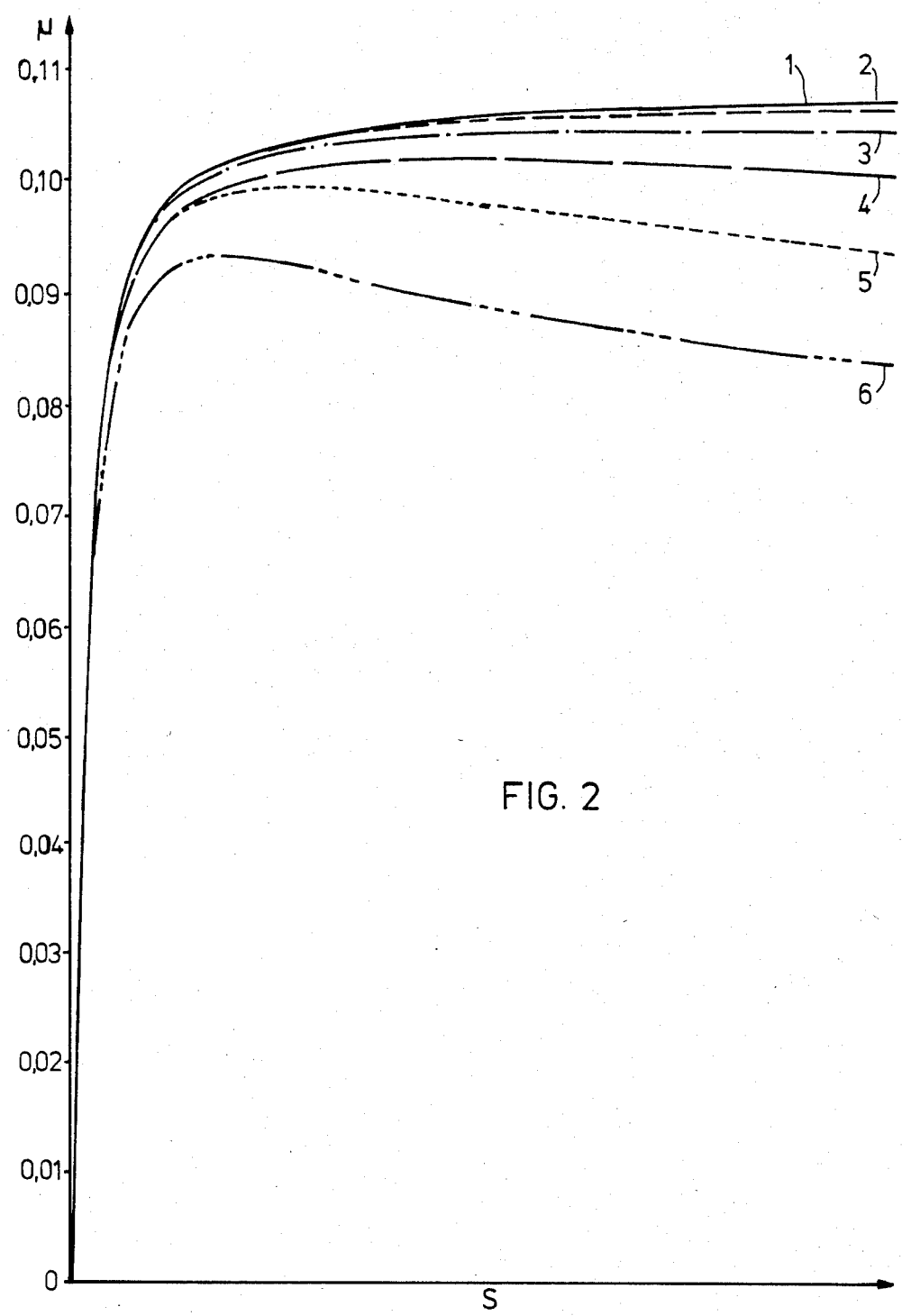
Figure 3:
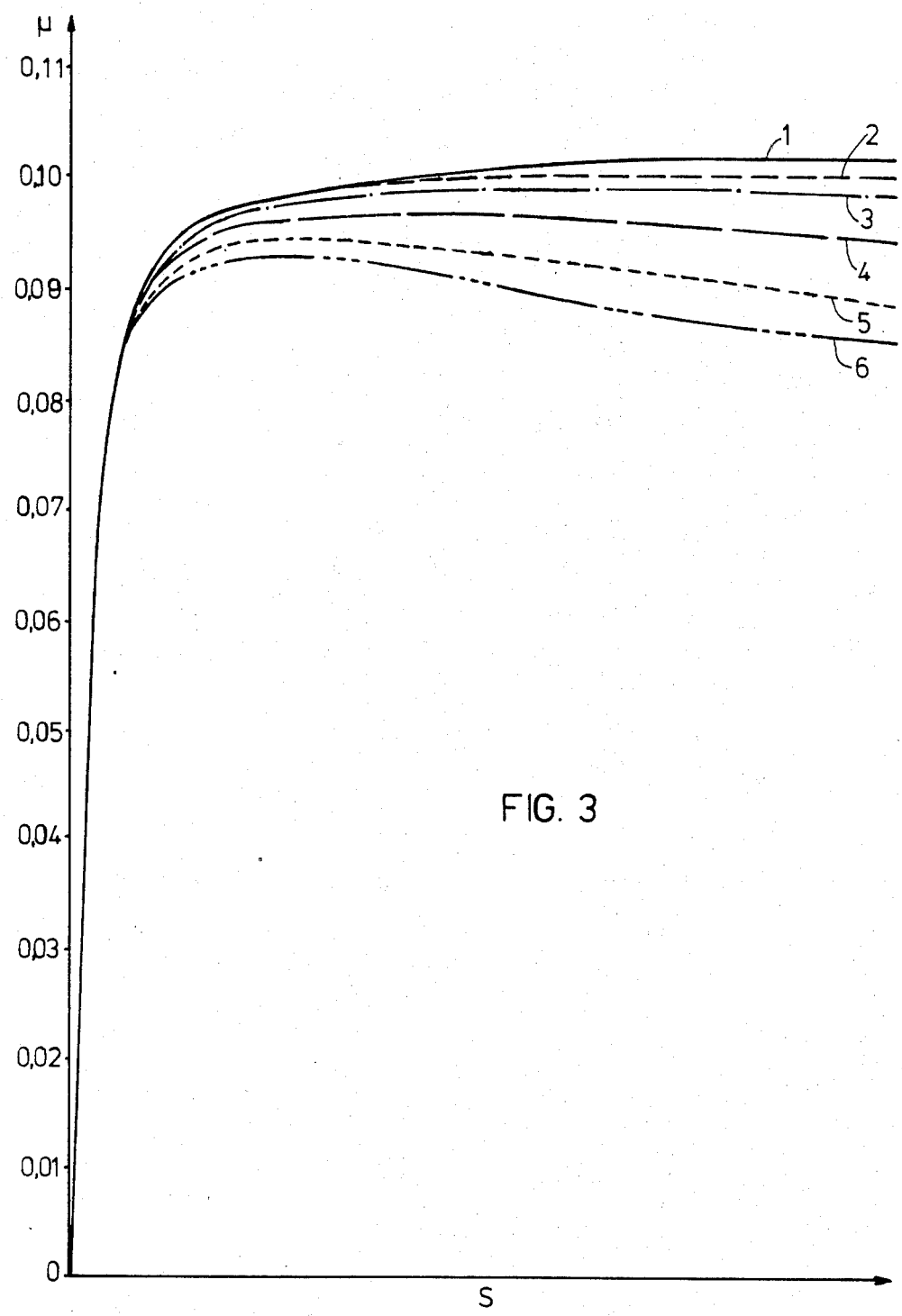
Figure 4:
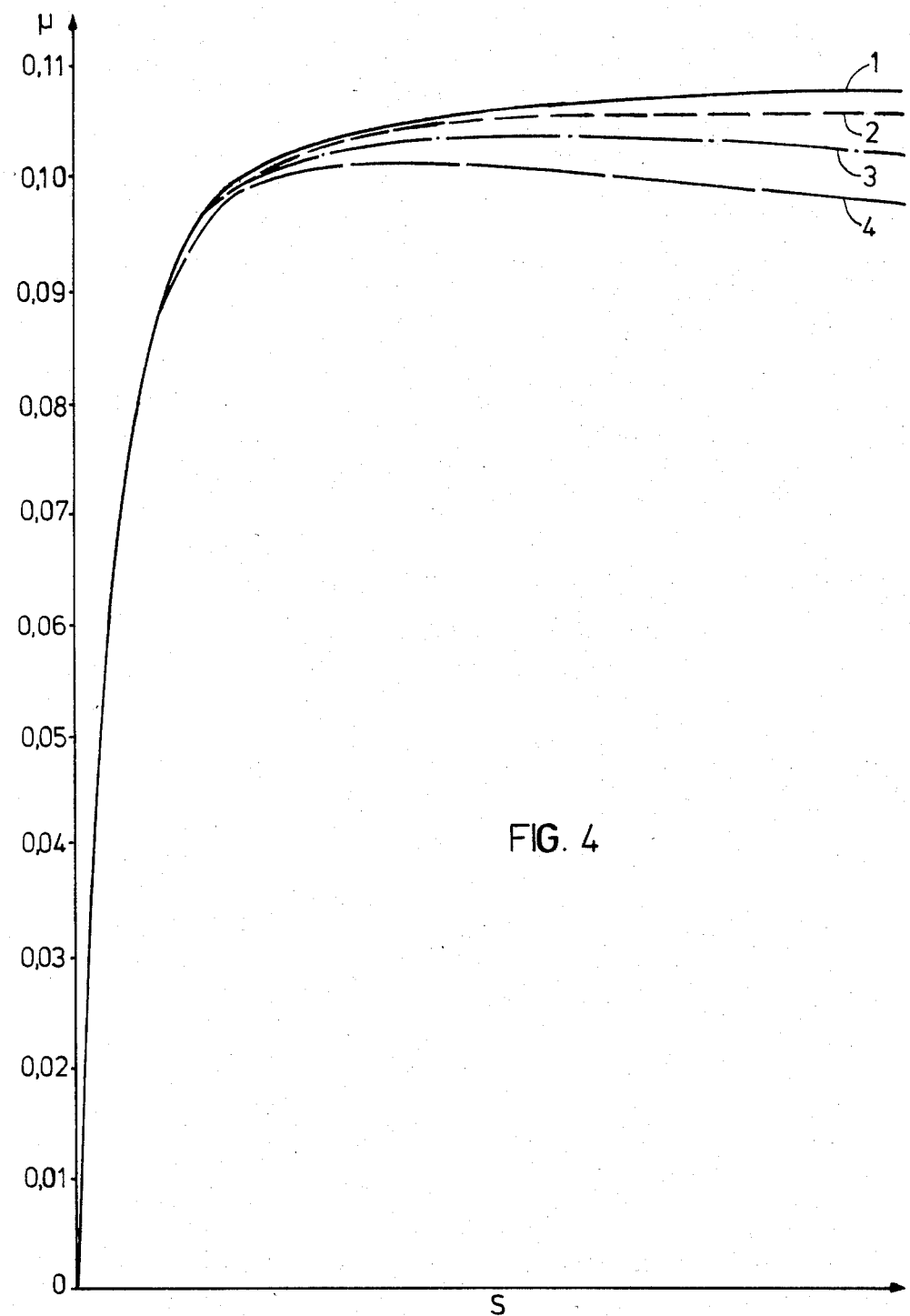

United States Patent [19]

Hentschel et al.

[11] Patent Number: 4,499,000

[45] Date of Patent: Feb. 12, 1985

[54] POWER-TRANSMISSION METHOD USES SPIROCYCLIC KETALS

[75] Inventors: Karl-Heinz Hentschel; Rolf Dhein, both of Krefeld; Hans Winter; Herbert Vojacek, both of Munich, all of Fed. Rep. of Germany

[73] Assignee: Bayer Aktiengesellschaft, Leverkusen, Fed. Rep. of Germany

[21] Appl. No.: 467,991

[22] Filed: Feb. 18, 1983

Related U.S. Application Data

[63] Continuation of Ser. No. 294,695, Aug. 20, 1981, abandoned.

[30] Foreign Application Priority Data

Sep. 6, 1980 [DE] Fed. Rep. of Germany ....... 3033658

[51] Int. Cl.³ .............................................. C09K 5/00
[52] U.S. Cl. ...................... 252/73; 549/332; 74/690; 74/194; 549/341
[58] Field of Search .............. 252/73; 260/338, 340.9, 260/340.7; 74/690, 194

[56] References Cited

U.S. PATENT DOCUMENTS 4,354,028 10/1982 Martin et al. .................... 252/73

Primary Examiner—John D. Welsh
Attorney, Agent, or Firm—Sprung, Horn, Kramer & Woods

[57] ABSTRACT

Certain spirocyclic ketals of the formula

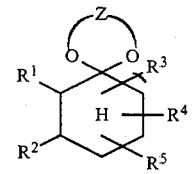

in which
R$^1$ in the case where R$^2$ denotes hydrogen, represents a cyclohexyl radical optionally substituted by lower alkyl, lower alkoxy and/or cycloalkyl with 5 to 7 carbon atoms, or in which
R$^1$ and R$^2$ are linked through 4 methylene groups, which are optionally substituted by lower alkyl, lower alkoxy and/or cycloalkyl with 5 to 7 carbon atoms and form a further acyclic ring.
R$^3$, R$^4$ and R$^5$ are identical or different and denote hydrogen, lower alkyl, lower alkoxy or cycloalkyl with 5 to 7 carbon atoms, and
Z denotes alkylene with 2 to 4 carbon atoms which is optionally substituted by lower alkyl and/or cycloalkyl with 5 to 7 carbon atoms, are disclosed together with their use in power transmission fluids.

9 Claims, 4 Drawing Figures

POWER-TRANSMISSION METHOD USES SPIROCYCLIC KETALS

This is a continuation of application Ser. No. 294,695, filed Aug. 20, 1981, abandoned.

The invention relates to power-transmission fluids containing cyclic ketals which are derived from alicyclic ketones.

In lubricated traction drives special fluids are required with the aid of which the torque of the driving element is transmitted to the driven element. Traction drive fluids and methods of testing them are known and are described for example in German Auslegeschrift No. 1,644,926; German Offenlegungsschrifts Nos. 1,925,826 and 2,506,735, Swiss Pat. No. 2,171,988, U.S. Pat. Nos. 3,394,603, 3,595,796, 3,597,358 and 3,997,617.

In order to transmit tractional forces between the driving element and the driven element a liquid film consisting of a lubricant is required in the zone of contact between the two roller elements, which is subjected to shearing for the transmission of the tractional forces.

In the assessment of the suitability of fluids as power transmitting fluids the coefficient of traction and the degree of slip which occurs when the circumferential speeds of the driving and driven elements are different during power transmission (Konstruktion 31, 2 to 6 and 55 to 62 (1979)) is significant.

When applied to traction drives the coefficient of traction is essentially determined by the slip, by the circumferential speed of the driving element and the normal force transmitted between the driving and the driven elements.

The coefficient of traction is defined as being the quotient of the traction due to the transmission of the traction between the driving and driven elements and the normal force (also called normal load) between the driving and driven elements. The slip is defined as being the absolute value of the quotient of the difference between the two circumferential speeds of the roller elements and the greater circumferential speed.

In the case of traction drives it is preferred that the coefficient of traction increases rapidly within a small range of slip (here a slip of less than 5% is meant). By means of this high efficiency of the traction drive is achieved.

In addition the maximum coefficient of traction is preferably as high as possible in order to achieve maximum power transmission.

In German Auslegeschrift No. 1,644,926 organic condensed saturated compounds are mentioned as power transmission fluids, which compounds consist of 2 to 9 condensed rings with a total of 9 to 60 carbon atoms, it being possible for up to 8 of these atoms to be replaced by oxygen, nitrogen, phosphorus and/or silicon atoms. In German Auslegeschrift No. 1,644,926 decalin, 1,2'-hydrindane, perhydro phenanthrene, perhydro fluorene, perhydro fluorenthene, perhydro acenaphthene, cyclohexyl decalin, primary perhydro cyclopentadiene and methylene hydrophenanthrene are mentioned as particularly suitable power-transmission fluids.

New power-transmission fluids have been found which contain spirocyclic ketals of the formula (I)

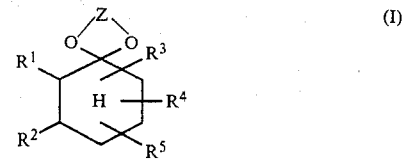

in which
R$^1$ in the case where R$^2$ denotes hydrogen, denotes a cyclohexyl radical optionally substituted by lower alkyl, lower alkoxy and/or cycloalkyl with 5 to 7 carbon atoms, or in which
R$^1$ and R$^2$ are linked through 4 methylene groups which are optionally substituted by lower alkyl, lower alkoxy and/or cycloalkyl with 5 to 7 carbon atoms and form a further alicyclic ring, R$^3$, R$^4$ and R$^5$ are identical or different and denote hydrogen, lower alkyl, lower alkoxy or cycloalkyl with 5 to 7 carbon atoms and Z denotes alkylene with 2 to 4 carbon atoms which is optionally substituted by lower alkyl and/or cycloalkyl with 5 to 7 carbon atoms.

The parent compounds of the spirocyclic ketals, which are derived from cyclohexyl-cyclohexanone and/or from 1-decalones can be substituted by lower alkyl, lower alkoxy and/or cycloalkyl with 4 to 7 carbon atoms.

According to the invention lower alkyl denotes a straight-chain or branched hydrocarbon radical with 1 to about 6 carbon atoms, Methyl, ethyl, propyl, isopropyl, butyl, isobutyl, pentyl, isopentyl, hexyl and isohexyl may be mentioned as examples.

According to the invention lower alkoxy denotes an aliphatic ether radical whose aliphatic part consists of a straight-chain or branched hydrocarbon radical with 1 to about 6 carbon atoms. The following alkoxy radicals may be mentioned as examples: methoxy, ethoxy, propoxy, isopropoxy, butoxy, isobutoxy, pentoxy, isopentoxy, hexoxy and isohexoxy.

Cycloalkyl with 5 to 7 carbon atoms represents cyclopentyl, cyclohexyl and cycloheptyl, preferably cyclohexyl.

Spirocyclic ketals of the formula (II)

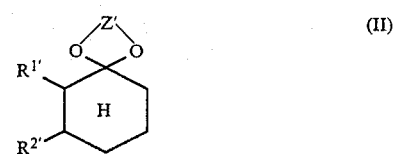

in which
R$^1$ in the case where R$^{2'}$ denotes hydrogen, represents a cyclohexyl radical,
or in which
R$^{1'}$ and R$^{2'}$ are linked through methylene groups and form a further alicyclic ring and
Z' represents the groups,
—CH$_2$—CH$_2$—,
—CH$_2$—CH$_2$—CH$_2$—,

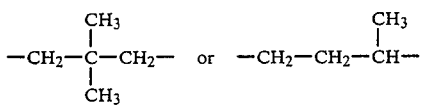

are the preferred power transmission fluids of the invention.

In particular, power transmission fluids are preferred which contain 7-cyclohexyl-1,5-dioxa-spiro (5.5)-undecane, 6-cyclohexyl-1,4-dioxa-spiro(4.5)-decane, 7-cyclohexyl-3,3-dimethyl-1,5-dioxa-spiro(5.5)-undecane or spiro-(1,3-dioxane-2.1')-decalin).

It is of course possible for the power transmission fluids according to the invention also to contain blend of the indicated spirocyclic ketals.

The spirocyclic ketals to be used according to the invention can be prepared by ketalization of substituted or preferably unsubstituted decalone or cyclohexyl-cyclohexanone with 1,2-, 1,3- or 1,4-alkanediols according to known methods of synthesis (Houben-Weyl VI/3 204–270 (1966) and Houben Weyl VII/1, 413–488 (1954)):

Unsubstituted or substituted decal-1-ones are readily obtainable from the corresponding 1-naphthols by complete hydrogenation with subsequent oxidation of the secondary alcohols to give the ketones. The corresponding α-naphthols can be substituted by lower alkyl radicals ($C_1$ to about $C_6$) or by $C_5$-$C_7$-cycloalkyl radicals. The following 1-decalones may be mentioned as examples: 1-naphthol, methyl-1-naphthols such as 2-methyl-1-naphthol, 4-methyl-1-naphthol, dimethyl-1-naphthols such as 2,4-dimethyl-1-naphthol, 5,8-dimethyl-1-naphthol, isobutyl-1-naphthols such as -isobutyl-1-naphthol, 4-isobutyl-1-naphthol, cyclopentyl-1-naphthols such as 2-cyclopentyl-1-naphthol, 4-cyclopentyl-1-naphthol and cyclohexyl-1-naphthols such as 2-cyclohexyl-1-naphthol and 4-cyclohexyl-1-naphthol.

Unsubstituted decal-1-one, which is readily accessible from 1-naphthol is preferred.

All aldol condensation products, which have been hydrogenated to give the saturated ketone, of two cyclohexanones, which are optionally substituted by lower alkyl ($C_1$ to about $C_6$), lower alkoxy ($C_1$ to about $C_6$) or cyclohexyl with 5 to 7 carbon atoms can be used as the 2-cyclohexyl-cyclohexanones, as long as at least one of the starting cyclohexanones contains at least one free methylene group adjacent to the carbonyl group.

Cyclohexanones, which can be used as starting products for the sprioycyclic ketals according to the invention are known per se (Beilstein, System No. 612, Vol. 7, Main Vol. 8 to 32, I6 to 27, II5 to 36, III 14 to 134.

They first have to be converted into substituted 2-cyclohexyl cyclohexanones by an aldol condensation reaction followed by partial hydrogenation.

The following cyclohexanones may be mentioned as examples: Methylcyclohexanones such as 2-methylcyclohexanones, 3-methylcyclohexanones, such as 3,4- and 3,5-dimethyl-cyclohexanones, 4-methylcyclohexanones, dimethyl-cyclohexanones, 4,4-dimethylcyclohexanones (with the exception of 2,6-dimethyl- cyclohexanone) and 3,3,5-trimethylcyclohexanone.

Unsubstituted 2-cyclohexyl-cyclohexanone is especially preferred as cyclohexanone to be katalized, which is particularly readily accessible from the 2-cyclohexenyl-2-cyclo-hexylidene-cyclohexanone mixture obtained as a by-product of the industrial preparation of adipic acid by oxidation of cyclohexanol/cyclohexanone mixtures.

Alkanediols for the preparation of the spirocyclic ketals are known per se (Houbel-Weyl VI 13, 213–220 (1966)).

The following alkanediols may be mentioned as examples: ethylene glycol, 1,3-propanediol, 1,2-propanediol, 1,2-, 1,3-, 1,4-butanediol, 1,2-, 1,3-, 1,4-, 2,3- or 2,4-pentanediol, 2,2-dimethyl 1,3-propanediol, 2-methyl-2-ethyl-1,3-propanediol, 2-methyl-2-propyl-1,3-propanediol, 2-methyl-2-butyl-1,3-propanediol and $C_6$–$C_{12}$-alkanediols in which the two hydroxyl groups are separated from one another by 2 to 4 carbon atoms between them.

According to a preferred ketalization process the ketone is reacted with an equimolar mixture of a lower alkyl orthocarboxylate, e.g. trimethyl orthoformate, and the alkanediol, in which, after heating, the desired spirocyclic ketal is formed in particularly good yields, under acid catalysis and with lower alkyl monoalcohols and lower alkyl carboxylates being split off.

The preparation of the spirocyclic ketals is generally conducted within a temperature range of from 20° to 250° C., preferably 50° to 100° C.

It may be advantageous to carry out the ketalisation in the presence of catalytic amounts of an acid, e.g. sulphuric acid.

The spirocyclic ketals are outstandingly suitable according to the invention, as power transmission fluids for traction drives. The following traction drives may be mentioned as examples of the application of the power transmission fluids according to the invention: Flexible drive mechanisms such as sliding link chain drives and roller chain drives, and rolling contact drive mechanisms such as ball and disc drives, roller and toroid drives and ball and roller drives.

The highest utilizable coefficients of traction in traction drives using the spirocyclic ketals as power transmission fluids are in general in the range of from 0.05 to 0.1, preferably from 0.065 to 0.09. Optimum power transmission in the drive mechanisms is thereby achieved. In comparison with commercially available power transmission fluids by means of the fluids according to the invention minimization of the dimensions of the drive mechanism is made possible.

In addition, the fluids according to the invention are marked by a particularly steep slope in the coefficients of traction at a slippage in the range of 0 to 1%. By means of this the losses in power transmission which can be kept very small. Consequently the frictional heating due to the power transmission remains low.

The spirocyclic ketals of the invention advantageously have a high resistance to heat and do not age even under great stress:

The viscosity indices of the spirocyclic ketals according to the invention are within a range of from −500 to +100, preferably −200 to +60. Since only low frictional heat is released, the viscosity of the fluid does not change considerably when used in the drive mechanism.

The spirocyclic ketals according to the invention also exhibit good lubricant properties. Therefore, when using them as power transmission fluids adequate lubrication of the drive mechanism is also at the same time provided.

The power transmission fluids according to the invention can also contain other components in addition to the spirocyclic ketals, depending on the field of application. In general the power transmission fluids according to the invention contain at least 50% by weight of a spirocyclic ketal. It is however also possible for them to consist of the practically pure spirocyclic ketal without further additives. Preferably, the power transmission fluids according to the invention contain 60 to 95% by weight of the spirocyclic ketal.

The possible additives to the spirocyclic ketals in the power transmission fluids depend essentially on the applicational fields. The preferred applicational fields for the power transmission fluids according to the invention are traction drives.

For use in traction drives the spirocyclic ketals according to the invention are in general the main component. Common additives are for example viscosity index improvers such as poly(meth)acrylate, polyisobutenes, hydrogenated styrene-dien block polymers and hydrogenated styrene-olefine copolymers, extreme-pressure and/or antiwear additives such as zinc dialkyl dithiophosphate, antioxidants such as alkylphenols, diarylamines, phenylene diamines, phenothiazines and organic phosphorus (III) compounds and dyestuffs such as azo dyes and triphenylmethane dyes.

The power transmission fluids for traction drives consist in general of 60 to 95 parts by weight of the spirocyclic ketal, with 0.1 to 15 parts by weight of the viscosity index improver, 0.1 to 5 parts by weight of the extreme pressure and/or antiwear additive and 0.01 to 3 parts by weight of the antioxidant. Preferred power transmission fluids for traction drives consist of 80 to 90 parts by weight of the spirocyclic ketal, 0.5 to 10 parts by weight of the viscosity index improver, 0.5 to 3 parts by weight of the extreme-pressure and/or antiwear additive and 0.05 to 2 parts by weight of the antioxidant.

In addition it is possible for the fluids to contain 0.01 to 1, preferably 0.05 to 0.5 parts by weight of a dyestuff.

In comparison with known commercially available power transmission fluids the power transmission fluids of the invention containing spirocyclic ketals exhibit considerably improved properties. This improvement in the properties was not forseeable from the prior art.

EXAMPLE 1

7-Cyclohexyl-1,5-dioxa-spiro [5.5]undecane 1,260 g (7 mols) of 2-cyclohexyl-cyclohexanone, together with 816.2 g (7.7 mols) of trimethylorthoformate, 585.2 g (7.7 mols) of dehydrated 1,3-propanediol and 7 drops of concentrated $H_2SO_4$ are refluxed, under a weak stream of nitrogen, in a 4 l three-necked flask with a stirrer, distillation column and distillation head with reflux regulator. During this procedure a mixture of methanol and methyl formate (a total of about 870 g) is slowly distilled over. The reaction mixture is then cooled, 3.5 g of anhydrous potassium carbonate are added and the mixture is boiled up for 10 minutes. After filtering, the product is fractionated first under a waterpump vacuum and then under an oil pump vacuum.

Yield: 968 g (58% of theory).
Boiling point$_1$=121° C., $n_D^{20}$=1.4946.
The elementary analysis and the NMR spectrum are in agreement with the structure and composition $C_{15}H_{26}O_2$.

| Kinematic viscosities: | at 37.8° C. (100° F.): 22.6 mm$^2$/s |
| --- | --- |
| | at 98.9° C. (210° F.)1: 3.39 mm$^2$/s |
| Viscosity index: | −53 |

Measurement of the coefficients of traction at 50° C. with a twin-disc machine at different normal forces and at different circumferential velocities give the following values:

| with a normal force of 125 N: | 0.987 (12.6 m/s)– |
| --- | --- |
| | 0.098 (0.84 m/s) |
| under a normal force of 700 N: | 0.098 (12.6 m/s)– |
| | 0.113 (0.84 m/s) |
| under a normal force 2,000 N: of | 0.097 (12.6 m/s)– |
| | 0.107 (0.84 m/s) |
| under a normal force 4,000 N: of | 0.107 (12.6 m/s)– |
| | 0.113 (0.84 m/s) |

This example illustrates the high coefficients of traction shown by the fluids according to the invention.

EXAMPLE 2

6-Cyclohexyl-1,4-dioxa-spiro [4.5]decane 1,260 g (7 mols) of 2-cyclohexyl-cyclohexanone are reacted with 816.2 g (7.7 mols) of trimethylorthoformate and 477.4 g (7.7 mols) of anhydrous 1,2-ethanediol in a manner analogous to that in Example 1.

Yield: 1,013 g (65% of theory).
Boiling point$_{0.4}$=99° C., $n_D^{20}$=1.4902
The elementary analysis and the NMR spectrum are in agreement with the structure and the composition $C_{14}H_{24}O_2$.

| Kinematic viscosities: | at 37.8° C. (100° F.): 9.82 mm$^2$/s |
| --- | --- |
| | at 98.9° C. (210° F.): 2.32 mm$^2$s |
| Viscosity index: | 37 |

Measurements of the coefficients of traction (as in Example 1):

| with a normal force of 2,000 N: | 0.085 (12.6 m/s)– |
| --- | --- |
| | 0.096 (0.84 m/s) |

EXAMPLE 3

7-Cyclohexyl-3,3-dimethyl-1,5-dioxa-spiro [5.5]undecane 1.170 g (6.5 mols) of 2-cyclohexyl-cyclohexanone are reacted with 757.9 g (7.15 mols) of trimethyl orthoformate and 743.6 g (7.15 mols) of anhydrous 2,2-dimethyl-1,3-propanediol in a manner analogous to that in Example 1:

Yield: 1,230 g (71% of theory)
Boiling point$_{0.3}$=122° C., $n_D^{20}$=1.4880
The elementary analysis and the NMR spectrum are in agreement with the structure and the composition $C_{17}H_{30}O_2$.

| Kinematic viscosities: | at 37.8° C. (100° F.): 55.2 mm$^2$/s |
| --- | --- |
| | at 98.9° C. (210° F.): 3.94 mm$^2$/s |
| Viscosity index: | −474 |

Measurements of the coefficients of traction (as in Example 1):

| at a normal force of 2,000 N: | 0.099 (12.6 m/s)– |
| --- | --- |
| | 0.108 (0.84 m/s) |
| at a normal force of 4,000 N: | 0.098 (12.6 m/s)– |
| | 0.102 (0.84 m/s) |

EXAMPLE 4

Spiro-(1,3-dioxane[2.1']decalin)

1,444 g (9.5 mols) of decal-1-one are reacted with 1,107.7 g (10.45 mols) of trimethyl orthoformate and 794.2 g (10.45 mols) of 1,3-propanediol in a manner analogous to that in Example 1.

Yield: 1,292 g (65% of theory).

Boiling point$_{1.2}$=103° C., $n_D^{20}$=1.4944

The elementary analysis and the NMR spectrum are in agreement with the structure and the composition $C_{13}H_{22}O_2$.

| Kinematic viscosities: | at 37.8° C. (100° F.): 877 mm$^2$/s |
| --- | --- |
|  | at 98.9° C. (210° F.): 2.24 mm$^2$/s |
| viscosity index: | 60 |

Measurements of the coefficients of traction (as in Example 1):

| at a normal force of 125 N: | 0.073 (12.6 m/s)–0.092 (0.84 m/s) |
| --- | --- |
| at a normal force of 700 N: | 0.087 (12.6 m/s)–0.106 (0.84 m/s) |
| at a normal force of 2,000 N: | 0.083 (12.6 m/s)–0.100 (0.84 m/s) |
| at a normal force of 4,000 N: | 0.087 (12.6 m/s)–0.102 (= .84 m/s) |

EXAMPLE 5

7-Cyclohexyl-2-methyl-1,6-dioxane-spiro (5.5)undecane 1260 g (7 mols) of 2-cyclohexyl-cyclohexanone, together with 816.2 g (7.7 mols) of trimethylorthoformate, 693.0 g (7.7 mols) of dehydrated 1,3-butanediol (7.7 mols) and 7 drops of concentrated sulphonic acid are refluxed under a weak stream of nitrogen in a 4 l three-necked flask with a stirrer distillation column and distillation head with reflux regulator. During this procedure a mixture of methanol and methyl formate (a total of about 870 g) is slowly distilled over. The reaction mixture is then cooled, 3.5 g of anhydroux potassium carbonate are added and the mixture is heated again for 10 minutes. After filtering the product is fractionated first under a waterpump vacuum and then under an oil pump vacuum.

Yield: 1077 g (61% of theory);

Boiling Point=105° C., $n_D^{20}$=1.4852

The elementary analysis and the NMR spectrum are in agreement with the structure and the composition CHO.

| Kinematic viscosities: | at 87.8° C.: 20.6 mm$^2$/s |
| --- | --- |
|  | at 98.9° C.: 2.91 mm$^2$/s |
| Viscosity index: | 183 |

Measurements of the coefficients of traction (as in Example 1):
at a normal force of 125 N:
at a normal force of 700 N:
at a normal force of 2,000 N:
at a normal force of 4,000 N:

EXAMPLE 6

The influence of the circumferential velocity (v), the slips between two discs and the normal force $F_N$ transmitted in the contact on the coefficient of traction (μ) is determined with a twin-disc machine (as described by K. Stoessel (Konstruktion 31 (1979) pages 4 and 5)).

The discs consist of a material which is described according to DIN 17006 with 100 Cr 6. The discs have a diameter of 80 μm, that of the driven disc 0.065 μm.

The fluid according to Example 1 is injected between the two discs with a temperature of 50° C. and a viscosity of 10.0 Pas.

In FIGS. 1 to 4 the dependence of the coefficient of traction on the slip is determined as a function of the normal force (also called normal load) and the circumferential speed of the driving disc.

The results shown in the following figures were performed at the following normal forces:

FIG. 1: $F_N$=125 N
FIG. 2: $F_N$=700 N
FIG. 3: $F_N$=2000 N
FIG. 4: $F_N$=4080 N

In addition the circumferential speeds of the driving element were varied in each test. The following notations correspond to the following circumferential speeds:

1. v=0.42 m/s
2. v=0.84 m/s
3. v=2.10 m/s
4. v=4.19 m/s
5. v=8.38 m/s
6. v=12.57 m/s

The results show a very steep increase of the coefficient of traction at a low slip and very high values for the coefficient of traction. Consequently a very good efficiency of the traction drive can be achieved.

What is claimed is:

1. A method of transmitting torque or tractional forces from a tractional driving element to a driven element through a traction fluid comprising using as said fluid a composition comprising a spirocyclic ketal of the formula (I)

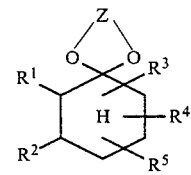

in which
R$^1$ in the case where R$^2$ denotes hydrogen, represents a cyclohexyl radical optionally substituted by lower alkyl, lower alkoxy and/or cycloalkyl with 5 to 7 carbon atoms, or in which
R$^1$ and R$^2$ are linked through 4 methylene groups, which are optionally substituted by lower alkyl, lower alkoxy and/or cycloalkyl with 5 to 7 carbon atoms and form a further acyclic ring;
R$^3$, R$^4$ and R$^5$ are identical or different and denote hydrogen, lower alkyl, lower alkoxy or cycloalkyl with 5 to 7 carbon atoms, and
Z denotes alkylene with 2 to 4 carbon atoms which is optionally substituted by lower alkyl and/or cycloalkyl with 5 to 7 carbon atoms.

2. A process according to claim 1, wherein said traction fluid contains at least 50% by weight of said spirocyclic ketal.

3. A process according to claim 1, wherein said traction fluid contains 60 to 95% by weight of said spirocyclic ketal.

4. Method according to claim 1, wherein said spirocyclic ketal is 7-cyclohexal-1,5-dioxaspirol [5.5] undecane.

5. Method according to claim 1, wherein said spirocyclic ketal is 6-cyclohexyl-1,4-dioxaspirol [4.5] decane.

6. Method according to claim 1, wherein said spirocyclic ketal is 7-cyclohexyl-3,3-dimethyl-1,5-dioxaspiro [5.5] undecane.

7. Method according to claim 1, wherein said spirocyclic ketal is spiro-(1,3-dioxane [2.1'] decalin).

8. Method according to claim 1, wherein said spirocyclic ketal is 7-cyclohexyl-2-methyl-1,5-dioxane-spiro (5.5) undecane.

9. Method according to claim 1, wherein said spirocyclic ketal is present in admixture with a diluent.

* * * * *